(12) United States Patent
Ackley et al.

(10) Patent No.: US 9,211,657 B2
(45) Date of Patent: Dec. 15, 2015

(54) SURGICAL TISSUE SEALER

(71) Applicant: COVIDIEN LP, Mansfield, MA (US)

(72) Inventors: Joanna Ackley, Boulder, CO (US); James D. Allen, IV, Broomfield, CO (US); Ryan C. Artale, Boulder, CO (US); Kim V. Brandt, Loveland, CO (US); Dennis W. Butcher, Longmont, CO (US); Edward M. Chojin, Boulder, CO (US); Gary M. Couture, Longmont, CO (US); James S. Cunningham, Boulder, CO (US); David M. Garrison, Longmont, CO (US); Keir Hart, Lafayette, CO (US); Russell D. Hempstead, Lafayette, CO (US); Glenn A. Horner, Boulder, CO (US); Daniel A. Joseph, Golden, CO (US); Duane E. Kerr, Loveland, CO (US); Dylan R. Kingsley, Broomfield, CO (US); Peter M. Mueller, Frederick, CO (US); Jessica E. C. Olson, Frederick, CO (US); Sean T. Oneill, Los Gatos, CA (US); Jason T. Sanders, Boulder, CO (US); Robert M. Sharp, Boulder, CO (US); John R. Twomey, Superior, CO (US); Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 61 days.

(21) Appl. No.: 14/297,316

(22) Filed: Jun. 5, 2014

(65) Prior Publication Data
US 2014/0284841 A1 Sep. 25, 2014

Related U.S. Application Data

(62) Division of application No. 13/412,897, filed on Mar. 6, 2012, now Pat. No. 8,752,264.

(51) Int. Cl.
*A61B 18/14* (2006.01)
*B29C 31/00* (2006.01)
(Continued)

(52) U.S. Cl.
CPC ........... *B29C 31/008* (2013.01); *A61B 18/1442* (2013.01); *A61B 18/1445* (2013.01);
(Continued)

(58) Field of Classification Search
CPC .. B29C 31/00; A61B 18/1445; A61B 18/144; A61B 2019/30; A61B 2017/00526; A61B 18/0063; A61B 17/28; A61B 17/282; A61B 2017/2825; Y10T 29/49771; Y10T 29/498; Y10T 29/49895
See application file for complete search history.

(56) References Cited

U.S. PATENT DOCUMENTS

| D249,549 S | 9/1978 | Pike |
|---|---|---|
| D263,020 S | 2/1982 | Rau, III |

(Continued)

FOREIGN PATENT DOCUMENTS

| CA | 2590520 A1 | 11/2007 |
|---|---|---|
| CN | 201299462 | 9/2009 |

(Continued)

OTHER PUBLICATIONS

Heniford et al. "Initial Results with an Electrothermal Bipolar Vessel Sealer" Surgical Endoscopy (2000) 15:799-801.
(Continued)

*Primary Examiner* — David Bryant
*Assistant Examiner* — Jun Yoo

(57) ABSTRACT

A method for manufacturing an end effector assembly includes providing first and second jaw members moveable relative to one another about a pivot between a first, spaced-apart position and a second, approximated position. One of the first and second jaw members includes a cavity defined therein and the other of the first and second jaw members includes a stop member configured to be inserted into the cavity. A gap-setting gauge is grasped between the first and second jaw members to define a gap-distance between the jaw members equivalent to a thickness of the gap-setting gauge. The first and second jaw members are set such that the jaw members are prevented from approximation beyond the gap-distance.

4 Claims, 5 Drawing Sheets

(51) Int. Cl.
  *A61B 17/00* (2006.01)
  *A61B 18/00* (2006.01)
  *A61B 19/00* (2006.01)
(52) U.S. Cl.
  CPC .................. *A61B2017/00526* (2013.01); *A61B 2018/0063* (2013.01); *A61B 2019/304* (2013.01); *Y10T 29/4984* (2015.01); *Y10T 29/49771* (2015.01); *Y10T 29/49895* (2015.01)

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| 5,673,841 A | 10/1997 | Schulze et al. | |
| H1745 H | 8/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| 6,901,672 B1 | 6/2005 | Reilly | |
| D509,297 S | 9/2005 | Wells | |
| D525,361 S | 7/2006 | Hushka | |
| 7,083,618 B2 | 8/2006 | Couture et al. | |
| 7,090,673 B2 | 8/2006 | Dycus et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| D531,311 S | 10/2006 | Guerra et al. | |
| 7,118,587 B2 | 10/2006 | Dycus et al. | |
| 7,131,971 B2 | 11/2006 | Dycus et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinge | |
| D541,938 S | 5/2007 | Kerr et al. | |
| D545,432 S | 6/2007 | Watanabe | |
| D547,154 S | 7/2007 | Lee | |
| 7,255,697 B2 | 8/2007 | Dycus et al. | |
| D564,662 S | 3/2008 | Moses et al. | |
| D567,943 S | 4/2008 | Moses et al. | |
| 7,384,420 B2 | 6/2008 | Dycus et al. | |
| D575,395 S | 8/2008 | Hushka | |
| D575,401 S | 8/2008 | Hixson et al. | |
| D582,038 S | 12/2008 | Swoyer et al. | |
| 7,473,253 B2 | 1/2009 | Dycus et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,922,953 B2 | 4/2011 | Guerra | |
| D649,249 S | 11/2011 | Guerra | |
| D649,643 S | 11/2011 | Allen, IV et al. | |
| 8,128,624 B2 | 3/2012 | Couture et al. | |
| 8,752,264 B2 | 6/2014 | Ackley et al. | |
| 2002/0188294 A1 | 12/2002 | Couture et al. | |
| 2003/0018331 A1 | 1/2003 | Dycus et al. | |
| 2003/0229344 A1 | 12/2003 | Dycus et al. | |
| 2004/0049936 A1 | 3/2004 | Newman | |
| 2004/0082952 A1 | 4/2004 | Dycus et al. | |
| 2004/0087943 A1 | 5/2004 | Dycus et al. | |
| 2004/0116924 A1 | 6/2004 | Dycus et al. | |
| 2004/0243125 A1 | 12/2004 | Dycus et al. | |
| 2006/0084973 A1 | 4/2006 | Hushka | |
| 2006/0189981 A1 | 8/2006 | Dycus et al. | |
| 2006/0217709 A1 | 9/2006 | Couture et al. | |
| 2007/0062017 A1 | 3/2007 | Dycus et al. | |
| 2007/0074807 A1 | 4/2007 | Guerra | |
| 2007/0260242 A1 | 11/2007 | Dycus et al. | |
| 2009/0082767 A1 | 3/2009 | Unger et al. | |
| 2009/0171350 A1 | 7/2009 | Dycus et al. | |
| 2010/0179545 A1 | 7/2010 | Twomey et al. | |
| 2011/0162796 A1 | 7/2011 | Guerra | |
| 2011/0270252 A1 | 11/2011 | Horner et al. | |
| 2013/0018372 A1 | 1/2013 | Sims et al. | |

FOREIGN PATENT DOCUMENTS

| | | |
|---|---|---|
| DE | 2415263 A1 | 10/1975 |
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| EP | 1535581 | 6/2005 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |

(56) References Cited

FOREIGN PATENT DOCUMENTS

| JP | 11-192238 | A | 7/1999 |
|---|---|---|---|
| JP | 11244298 | A | 9/1999 |
| JP | 2000-102545 | A | 4/2000 |
| JP | 2000342599 | A | 12/2000 |
| JP | 2000350732 | A | 12/2000 |
| JP | 2001-8944 | | 1/2001 |
| JP | 2001-29356 | | 2/2001 |
| JP | 2001128990 | A | 5/2001 |
| JP | 2001-190564 | A | 7/2001 |
| JP | 20013400 | | 11/2001 |
| JP | 2002-528166 | A | 9/2002 |
| JP | 2003245285 | A | 9/2003 |
| JP | 2004-517668 | A | 6/2004 |
| JP | 2004-528869 | A | 9/2004 |
| JP | 2011125195 | A | 6/2011 |
| SU | 401367 | A1 | 10/1973 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 02/080794 | | 10/2002 |
| WO | 02/080795 | | 10/2002 |
| WO | 02/080796 | | 10/2002 |
| WO | 02/080799 | | 10/2002 |
| WO | 2004/073490 | A2 | 9/2004 |
| WO | 2005/110264 | A2 | 11/2005 |

OTHER PUBLICATIONS

Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.

(56) References Cited

OTHER PUBLICATIONS

U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/USO4/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5. dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.

(56) References Cited

OTHER PUBLICATIONS

U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Intl'Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.

SURGICAL TISSUE SEALER

CROSS-REFERENCE TO RELATED APPLICATIONS

The present application is a division of U.S. application Ser. No. 13/412,897, filed on Mar. 6, 2012, the entire contents of which are hereby incorporated by reference herein.

BACKGROUND

The present disclosure\ relates to surgical instruments and, more particularly, to a surgical tissue sealing for grasping, sealing and/or dividing tissue.

TECHNICAL FIELD

A forceps is a pliers-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

SUMMARY

According to one aspect of the present disclosure, a method for manufacturing an end effector assembly is provided. The method includes grasping a gap-setting gauge between first and second jaw members moveable relative to one another about a pivot between a first, spaced-apart position and a second position proximate tissue and setting the first and second jaw members such that in the approximated position the jaw members cooperate to define a gap distance between the jaw members equivalent to the thickness of the gap-setting gauge such that when positioning tissue between the jaw members full approximation of the jaws is limited to the gap distance.

According to another aspect of the present disclosure, a method for manufacturing an end effect assembly is provided. The method includes grasping a gap-setting gauge between first and second jaw members moveable relative to one another about a pivot between a first, spaced-apart position and a second position proximate tissue, inserting an adjustable stop member into at least one of the first and second jaw members, setting the first and second jaw members such that in the approximated position the jaw members cooperate to define a gap distance between the jaw members equivalent to the thickness of the gap-setting gauge, and securing the adjustable stop member to the at least one of the first and second jaw members such that when positioning tissue between the jaw members full approximation of the jaws is limited to the gap distance.

BRIEF DESCRIPTION OF THE DRAWINGS

Various embodiments of the present disclosure are described herein with reference to the drawings wherein.

DETAILED DESCRIPTION

Figure 1:
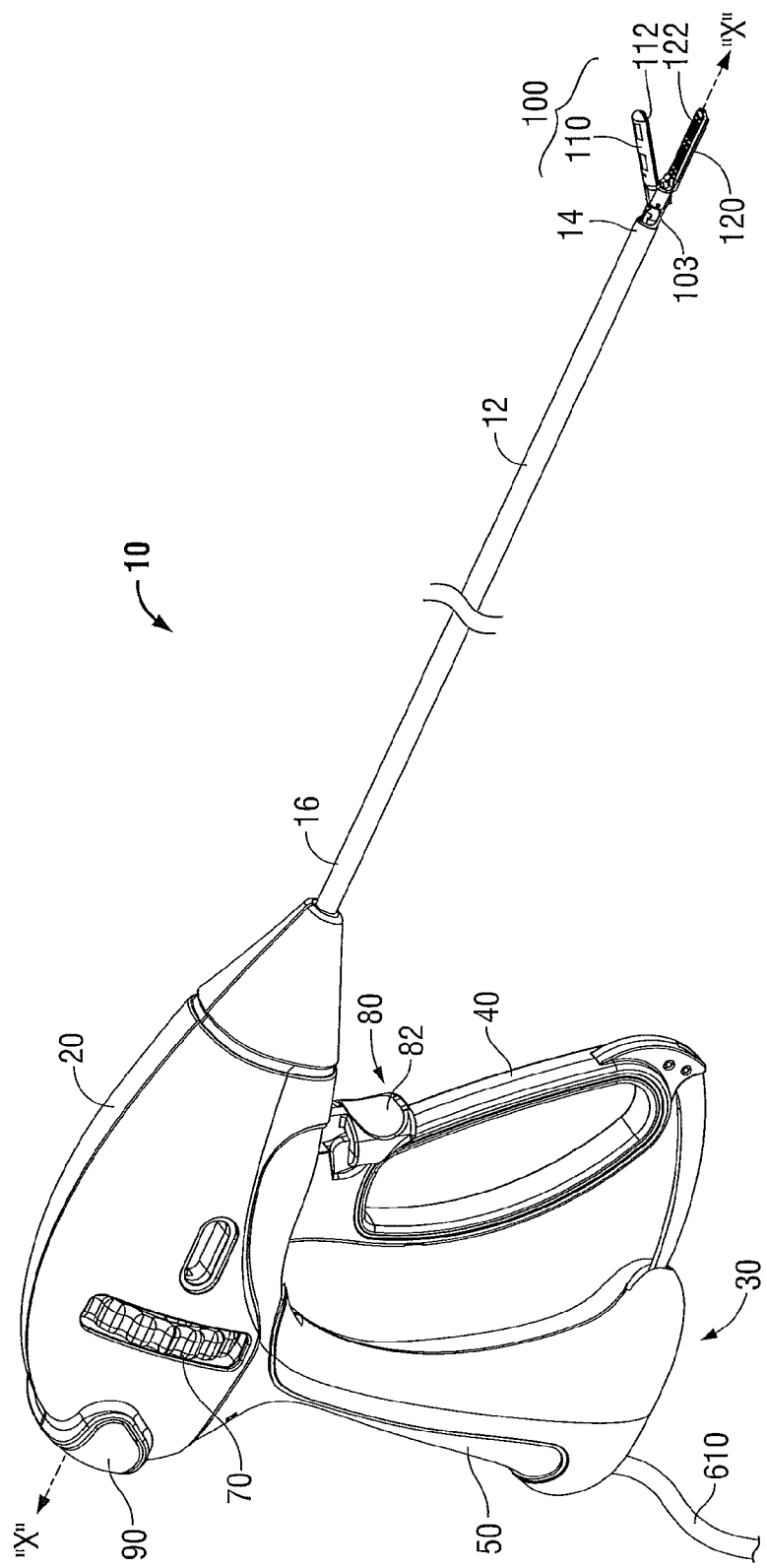
FIG. 1 is a front, perspective view of an endoscopic surgical instrument configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
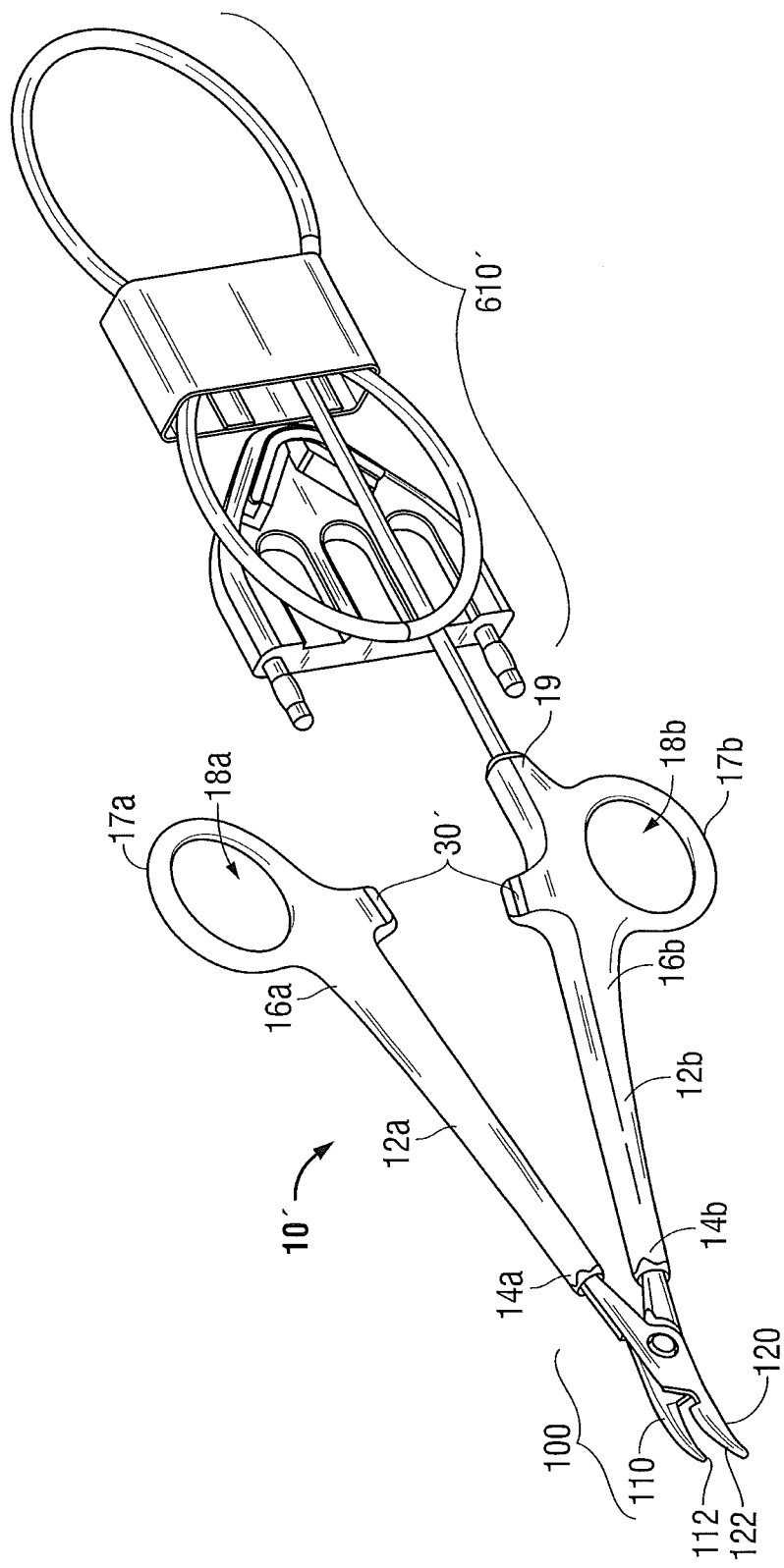
FIG. 2 is a front, perspective view of an open surgical instrument configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to at least one of the jaw members 110 and 120 of end effector assembly 100.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about a longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of jaw members 110 and 120 includes an opposed electrically conductive tissue sealing surface 112, 122, respectively. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12. In some embodiments, a knife assembly (not shown) is disposed within shaft 12 and a knife channel (not shown) is defined within one or both jaw members 110, 120 to permit reciprocation of a knife blade (not shown) therethrough, e.g., via activation of trigger 82 of trigger assembly 80. The particular features of end effector assembly 100 will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue disposed between sealing surfaces 112 and 122 of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that are pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another that, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. It is envisioned that the ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 which is designed to connect the forceps 10' to a source of electrosurgical energy such as an electrosurgical generator (not shown). Proximal shaft connector 19 secures an electrosurgical cable 610' to forceps 10' such that the user may selectively apply electrosurgical energy to the electrically conductive sealing surfaces 112 and 122 (FIG. 1) of jaw members 110 and 120, respectively, as needed.

Forceps 10' may further include a knife assembly (not shown) disposed within either of shafts 12a, 12b and a knife channel (not shown) defined within one or both jaw members 110, 120 to permit reciprocation of a knife blade (not shown) therethrough.

Figure 3:
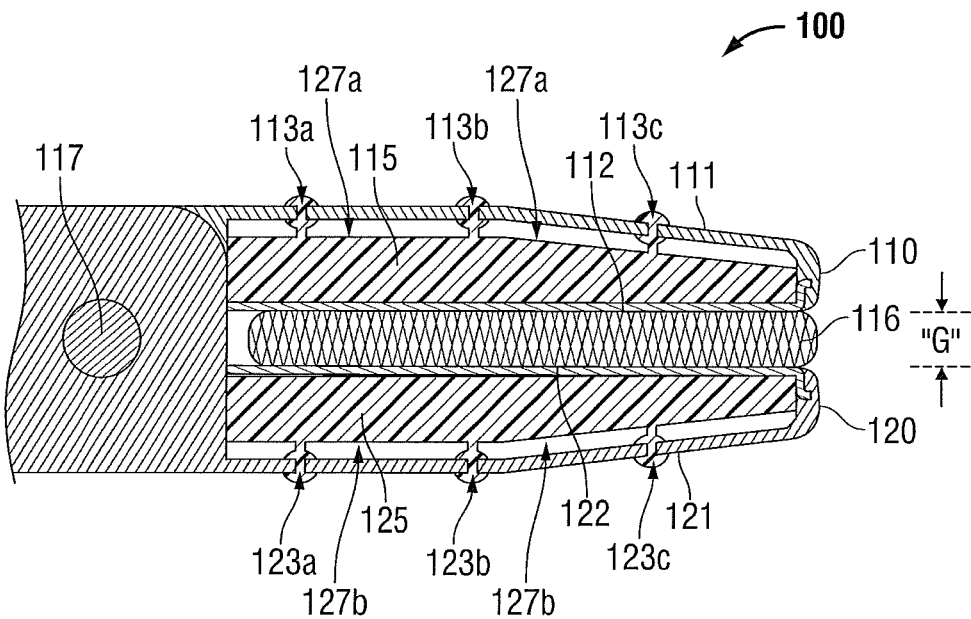
FIG. 3 is an enlarged, front, cross-sectional view of one embodiment of an end effector assembly configured for use with the surgical instrument of FIG. 1 or 2.

Turning now to FIG. 3, end effector assembly 100, including jaw members 110 and 120 is configured for use with either instrument 10 or instrument 10', discussed above, or any other suitable surgical instrument. However, for purposes of simplicity and consistency, end effector assembly 100 will be described hereinbelow with reference to instrument 10 only.

Tissue sealing procedures involve more than simply cauterizing tissue. In order to effect a proper seal in vessels or tissue, it has been determined that a variety of mechanical and electrical parameters should be accurately controlled: the pressure applied to the tissue; the gap distance between the electrodes (e.g., distance between opposing jaw members when closed about tissue); and amount of energy applied to tissue. In embodiments, the present disclosure provides for jaw members 110 and 120 that when fully approximated define a gap distance "G" from about 0.001 inches to about 0.006 inches as well as method for manufacturing the same. However, other gap distances are also contemplated by the present disclosure.

As shown in FIG. 3, each of the jaw members 110 and 120 includes a jaw housing 111 and 121, respectively. The sealing surfaces 112 and 122 are coupled to the housings 111 and 121 by overmolding or filling the housing 111 and 121 with a suitable material 115 and 125 that may assist in securing the sealing surfaces 112 and 122 thereto. The material 115 and 125 may be any suitable dielectric or insulating material that may be heat-staked through the housing 111 and 121 as described in further detail below. The housings 111 and 121 include one or more openings 113a and 113b and 123a and 123b, respectively, which are defined therein and are configured to received a material 115 and 125 therethrough for securing the materials 115 and 125 to the housing 111 and 121, respectively, as described in more detail below.

This configuration in combinations with any of the embodiments disclosed below in FIGS. 5-8 may also be used to set a desired gap distance "G." During assembly of the jaw members 110 and 120, the jaw members 110 and 120 grasp a gap-setting gauge 116 that provides for a desired gap distance "G." The material 115 and 125 is then heat staked on both sides of the housings 111 and 121, ultrasonically welded or otherwise secured through the openings 113a, 113b, 123a, 123b as the jaw members 110 and 120 grasp the gap-setting gauge 116 to permanently set the sealing surfaces 112 and 122 within the jaw members 110 and 120, respectively. The material 115 and 125 maintains gaps 127a and 127b within the housings 111 and 121, respectively. The gaps 127a and 127b allow for movement of the material 115 and 125 as well as the sealing surfaces 112 and 122 during the setting process to set the desired gap distance "G."

The jaw members 110 and 120 may be pivotally secured via a pin 117. Once jaw members 110 and 120 are disposed over the gap gauge 116, the pin 117 may be welded, flared, riveted, or otherwise secured to secure the jaw members 110 and 120.

Figure 4:
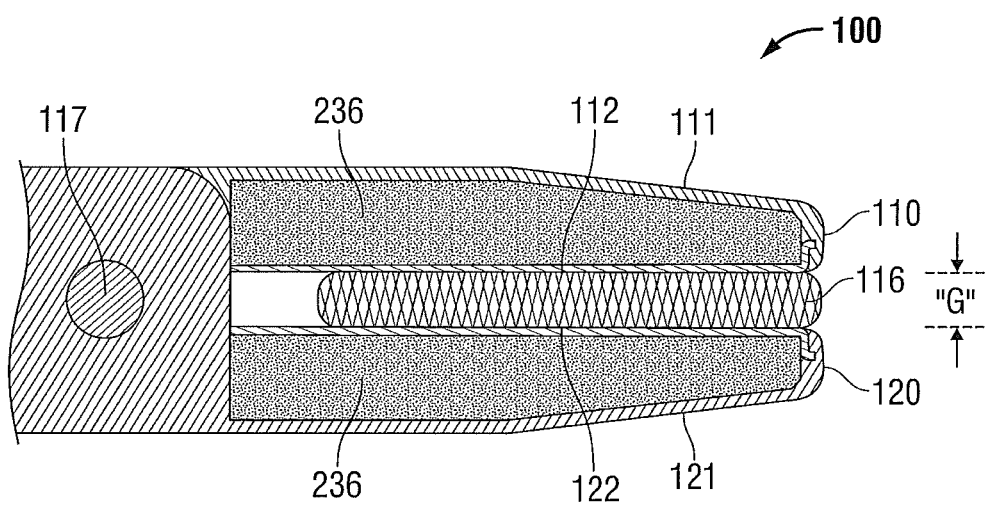
FIG. 4 is an enlarged, side, cross-sectional view of one embodiment of an end effector assembly configured for use with the surgical instrument of FIG. 1 or 2.

FIG. 4 shows an embodiment of setting the sealing surfaces 112 and 122 within the jaw members 110 and 120. The sealing surfaces 112 and 122 are coupled to the housings 111 and 121 by an adhesive material 236. The material 236 may be any liquid or amorphous material similar to the material 136 described above.

During assembly of the jaw members 110 and 120, the material 236 is deposited (e.g., injected) into the housings 111 and 121 and the jaw members 110 and 120 grasp the gap-setting gauge 116. The jaw members 110 and 120 are then fully approximated (e.g., handle 40 is fully squeezed and locked into handle assembly 30). The material 236 is allowed to cure and the jaw members 110 and 120 are now configured to provide a desired gap distance "G" therebetween. As the jaw members 110 and 120 grasp the gap-setting gauge 116, the material 236 solidifies to permanently set the sealing surfaces 112 and 122 within the jaw members 110 and 120. This configuration in combinations with any of the embodiments disclosed below in FIGS. 5-8 may also be used to set a desired gap distance "G."

Figure 5:
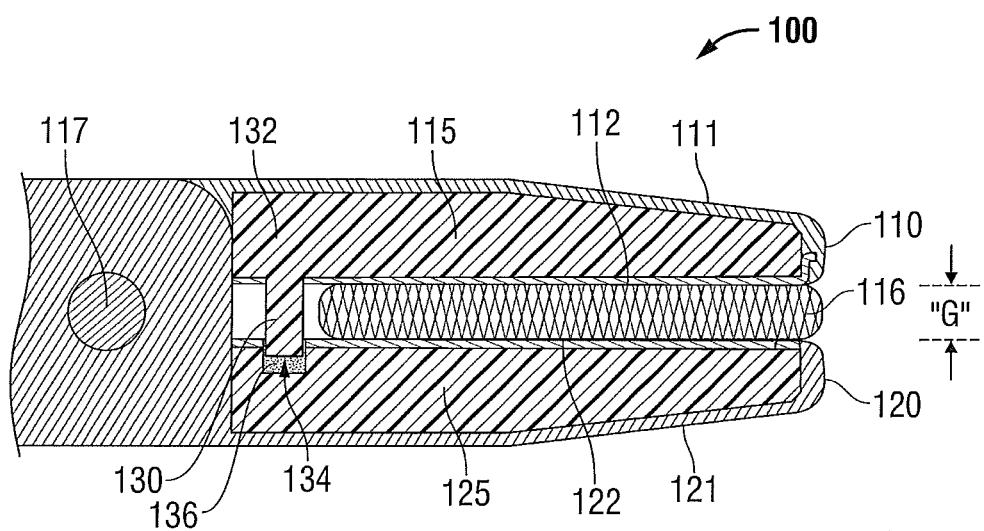
FIG. 5 is an enlarged, side, cross-sectional view of one embodiment of an end effector assembly configured for use with the surgical instrument of FIG. 1 or 2.

FIG. 5 shows another embodiment of a stop member configuration setting a gap distance "G" between the jaw members 110 and 120. As shown, the jaw member 110 includes a fixed stop member 130 disposed at a proximal portion 132 (e.g., closer to the pivot pin 117) of the jaw member 110. In some embodiments, the stop member 130 may be disposed on the jaw member 120. The stop member 130 is configured to be inserted into a cavity 134 defined within the jaw member 120. To obtain a desired gap distance "G," during assembly of the jaw members 110 and 120, the jaw members 110 and 120 grasp the gap-setting gauge 116 that provides for a desired gap distance "G." A setting material 136 is deposited into the cavity 134 to a sufficient level such that once the material 136 is solidified, it prevents approximation of the jaw members 110 and 120 beyond the gap distance "G." Once the material 136 has solidified, the jaw members 110 and 120 are permanently set to the desired gap distance "G" when in closed configuration as the travel distance for the stop member 130 is limited by the solidified material 136 (e.g., the jaw members 110 and 120 are able to freely rotate but bottom out at the appropriate gap distance "G" when the jaw member 110 comes in contact with the stop member 130).

The material 136 may be any liquid or amorphous material that solidifies upon deposition into the cavity 134. In some embodiments, the material 136 may be any material or combination of materials (e.g., epoxy) that may change its phase after deposition, such that the material 136 is initially in a liquid phase and then transitions into a solid phase.

In some embodiments, the material 136 may be a liquid material that may be solidified by one of the following processes which include, but are not limited to, room temperature vulcanization, a thermosetting polymer reaction (e.g., epoxy), curing (e.g., anaerobic or ultra-violet), and combinations thereof. The material 136 may be a polymer, which may include, but not limited to, polyesters, silicones, rubbers, epoxies, nylons, polyphthalamides, liquid crystal polymers, and combinations thereof.

Figure 6:
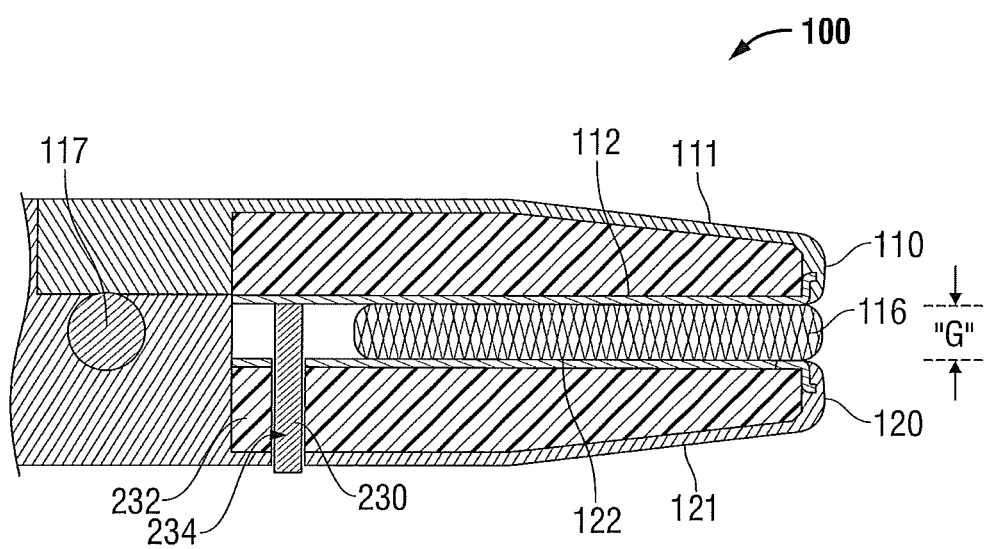
FIG. 6 is an enlarged, side, cross-sectional view of one embodiment of an end effector assembly configured for use with the surgical instrument of FIG. 1 or 2.

FIG. 6 shows another embodiment of a stop member configuration for setting a gap distance "G" between the jaw members 110 and 120. As shown, the jaw member 120 includes a stop member 230 disposed at a proximal portion 232 (e.g., closer to the pivot pin 117) of the jaw member 120. The stop member 230 may be disposed on the jaw member 110 and is configured to be inserted into an aperture 234 defined in the jaw member 120. To obtain a desired gap distance "G," during assembly of the jaw members 110 and 120, the jaw members 110 and 120 grasp the gap-setting gauge 116 that provides for a desired gap distance "G" and the stop member 230 is inserted through aperture 234. The stop member 230 is secured within the aperture such that the jaw members 110 and 120 are permanently set to the desired gap distance "G" when in the closed configuration (e.g., the jaw members 110 and 120 are able to freely rotate but bottom out at the appropriate gap distance "G" when the jaw member 110 comes in contact with the stop member 230).

Figure 7A:
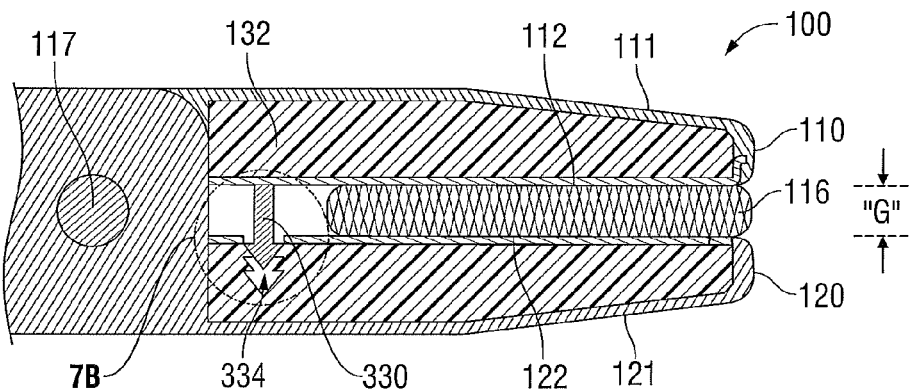
FIG. 7A is an enlarged, side, cross-sectional view of one embodiment of an end effector assembly configured for use with the surgical instrument of FIG. 1 or 2.
Figure 7B:
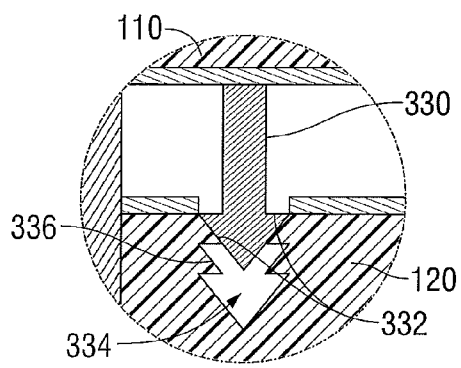
FIG. 7B is an enlarged view of the area of detail 7B of the end effector of FIG. 7A.
Figure 7C:
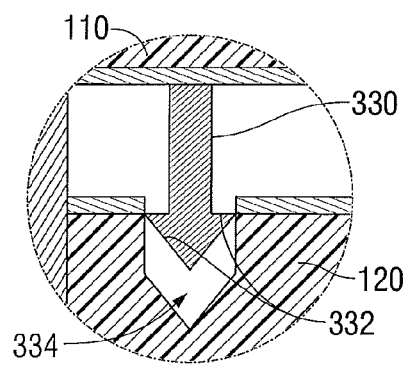
FIG. 7C is an enlarged view of the area of detail 7B of another embodiment of the end effector of FIG. 7A.

FIGS. 7A-7C shows another embodiment of setting a gap distance "G" between the jaw members 110 and 120. As shown, the jaw member 110 includes an adjustable stop member 330 disposed at a proximal portion 132 (e.g., closer to the pivot pin 117) of the jaw member 110. In some embodiments, the stop member 330 may be disposed on the jaw member 120. The stop member 330 is configured to be inserted into an aperture 334 through the jaw member 120. Each of the stop member 330 and aperture 334 include one or more surface features 332 and 336, respectively. The surface features 332 and 336 are configured to interlockingly engage with each other, such that the stop member 330 may only be inserted into the aperture 334 and is locked therein preventing extraction thereof. The stop member 330 is removably coupled (e.g., via peelable adhesive) to the jaw member 110 allowing the jaw members 110 and 120 to open, retaining the stop member 330 within the jaw member 120. Suitable surface features 332 and 336 include, but are not limited to, barbs, hooks, latches, protrusions, leaves, teeth and/or combinations thereof. In another embodiment, as shown in FIG. 7C, the aperture 334 may have a straight interference fit, without any surface features 336. Thus, the stop member 330 is inserted into the aperture 334 to a desired depth depending on the thickness of the gap-setting gauge 116. Once inserted to a desired depth, the surface features 332 and 336 interlock and set a specific gap "G."

To obtain a desired gap distance "G," during assembly of the jaw members 110 and 120, the jaw members 110 and 120 grasp the gap-setting gauge 116 therebetween and pressure is applied to the jaw members 110 and 120 until the surface features 332 and 336 engage each other. If more than one set of surface features 336 are used, the jaw members 110 and 120 may be approximated until a desired gap distance "G" is achieved.

Figure 8:
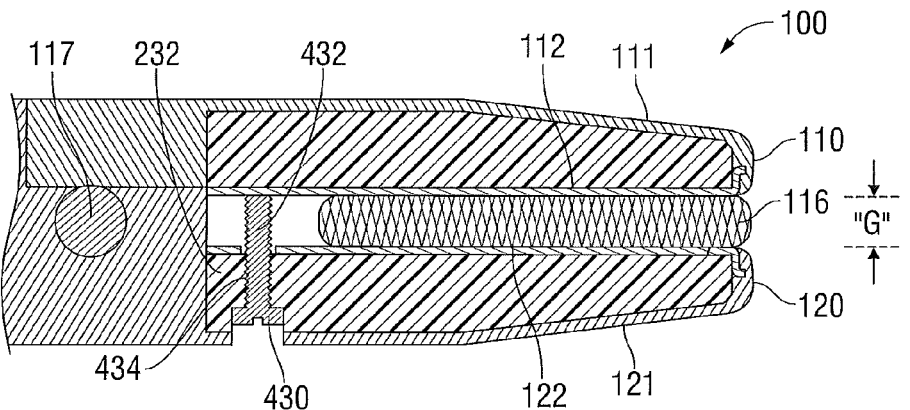
FIG. 8 is an enlarged, side, cross-sectional view of one embodiment of an end effector assembly configured for use with the surgical instrument of FIG. 1 or 2.

FIG. 8 shows another embodiment of a stop member configuration for setting a gap distance "G" between the jaw members 110 and 120. As shown, the jaw member 120 includes a stop member 430 disposed at a proximal portion 232 (e.g., closer to the pivot pin 117) of the jaw member 120. The stop member 430 may be disposed on the jaw member 120 and is configured to be inserted into an aperture 434 defined in the jaw member 120. The stop member 430 includes a threaded shaft 432 configured to threadably interface with the aperture 434. The stop member 430 may be adjusted to a desired height by rotating the stop member 430 in either clockwise or counterclockwise direction move the stop member 430 into or out of the aperture 434, thereby adjusting the gap distance "G." To obtain a desired gap distance "G," during assembly of the jaw members 110 and 120, the jaw members 110 and 120 grasp the gap-setting gauge 116 that provides for a desired gap distance "G" and the stop member 430 is threadably inserted through aperture 434. The stop member 430 is secured within the aperture such that the jaw members 110 and 120 are permanently set to the desired gap distance "G" when in the closed configuration (e.g., the jaw members 110 and 120 are able to freely rotate but bottom out at the appropriate gap distance "G" when the jaw member 110 comes in contact with the stop member 430).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for manufacturing an end effector assembly, the method comprising: providing first and second jaw members moveable relative to one another about a pivot between a first, spaced-apart position and a second, approximated position, wherein one of the first and second jaw members includes a cavity defined therein and the other of the first and second jaw members includes a stop member and configured to engage the cavity upon movement of the jaw members from the spaced-apart position to the approximated position; grasping a gap-setting gauge between the first and second jaw members while allowing the stop member to engage the cavity, the gap-setting gauge defining a gap-distance between the jaw members equivalent to a thickness of the gap-setting gauge; and fixing the first and second jaw members such that the jaw members are prevented from approximating beyond the gap-distance.

2. The method according to claim 1, wherein fixing includes depositing a setting material into the cavity and allowing the setting material to engage the stop member and cure.

3. The method according to claim 2, wherein the setting material is a non-solid material deposited into the cavity to a sufficient level such that once the stop member is engaged within the cavity and the non-solid material solidifies the gap-distance is set to limit approximation of the jaw members.

4. The method according to claim 1, wherein the stop member is affixed to a proximal portion of the first jaw member and the cavity is defined in a proximal portion of the second jaw member.

* * * * *